United States Patent [19]

Biftu et al.

[11] Patent Number: 5,001,123
[45] Date of Patent: Mar. 19, 1991

[54] 2,5-DIARYL TETRAHYDROFURANS AND ANALOGS THEREOF AS PAF ANTAGONISTS

[75] Inventors: Tesfaye Biftu; Nirindar N. Girotra, both of Parlin; Robert L. Bugianesi, Colonia; Mitree M. Ponpipom, Branchburg; Soumya P. Sahoo, Edison; Chan H. Kuo, South Plainfield, all of N.J.

[73] Assignee: Merck & Co., Inc., Rahway, N.J.

[21] Appl. No.: 362,907

[22] Filed: Jun. 8, 1989

[51] Int. Cl.$^5$ ............... C07D 405/04; C07D 413/12; A61K 31/44; A61K 31/55
[52] U.S. Cl. .................. 514/235.2; 514/255; 514/318; 514/341; 514/342; 514/343; 514/336; 544/124; 544/360; 546/194; 546/278; 546/280; 546/281; 546/283
[58] Field of Search ............... 546/283, 278, 280, 281, 546/194; 544/124, 360; 514/235.2, 255, 318, 341, 342, 343, 33 L

[56] References Cited

U.S. PATENT DOCUMENTS

| | | | |
|---|---|---|---|
| 3,769,350 | 10/1973 | Perry et al. | 568/8 |
| 4,539,332 | 9/1985 | Biftu et al. | 514/461 |
| 4,595,693 | 5/1986 | Biftu et al. | 514/461 |
| 4,757,084 | 7/1988 | Biftu et al. | 514/438 |

FOREIGN PATENT DOCUMENTS

| | | | |
|---|---|---|---|
| 0144804 | 6/1985 | European Pat. Off. | 546/283 |
| 0154887 | 9/1985 | European Pat. Off. | 546/284 |
| 0199324 | 10/1986 | European Pat. Off. | 544/315 |
| 0217204 | 4/1987 | European Pat. Off. | 544/315 |

OTHER PUBLICATIONS

Chem. Abstracts, vol. 42, Abstract 5836e (1948).
Chem. Abstracts, vol. 79, Abstract 136925u (1973).
Chem. Abstracts, vol. 81, Abstract 135662k (1974).
Chem. Abstracts, vol. 83, Abstract 8676g (1975).
Chem. Abstracts, vol. 86, Abstract 16468v (1977).
Chem. Abstracts, vol. 90, Abstract 54746z (1979).
Chem. Abstracts, vol. 96, Abstract 122588a (1982).
Biftu, T., Hazra, G. B., Steveson, R., and Williams, J. R., Synthesis of Lignans, 2,3-diaroylbutanes, J. Chem. Soc., pp. 1147–1150 (1978).
Biftu, T., Hazra, G.B., Steveson, R., Synthesis of (+)-Deoxyschizandrin, J. Chem. Soc., pp. 2276–2281 (1979).
Hwang, S. B., Lam, M. H., Biftu, T., Beattie, T. R., Asghen, T. Y., Trans-2,5-bis-(3,4,5-trimethoxyphenyl) Tetrahydrofuran, J. Biol. Chem., vol. 260, No. 29, pp. 15639–15645 (Dec. 1985).
Sarkanen, K. V. and Wallis, A. F. A., Oxidative Dimerizations's of (E)- and (Z)-Isoeugenol (2-Methoxy-4-propenylphenol) and (E)- and (Z)-2,6-dimethoxy-4-propenyl-phenol, J. Chem. Soc., Perkin transactions, pp. 1869–1878 (1973).
Stevenson, R., Williams, J. R., Synthesis of Tetrahydrofuran Lignans, (+)-Galbelgin and (+)-Grandisin, Tetrahedron, vol. 33, pp. 285–288 (1977).

*Primary Examiner*—Alan L. Rotman
*Attorney, Agent, or Firm*—Curtis C. Panzer; Joseph F. DiPrima; Hesna J. Pfeiffer

[57] ABSTRACT

The present invention is directed to a specifically substituted tetrahydrofuran of the formula (I)

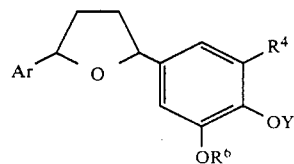

wherein Ar is a pyridyl, a dimethoxy-pyridyl or dimethoxy-pyrazyl group, $R^4$ is an alkylthio, alkylsulfinyl or alkylsulfonyl containing group and at least one of the substituents at positions 3,4 or 5 contains a heterocyclic, heteroaryl or substituted phenylthio group.

9 Claims, No Drawings

2,5-DIARYL TETRAHYDROFURANS AND ANALOGS THEREOF AS PAF ANTAGONISTS

BACKGROUND OF THE INVENTION

Platelet-activating factor (PAF) has recently been identified as an acetyl glyceryl ether phosphoryl-choline (AGEPC), i.e., 1-0 -hexadecyl/octadecyl-2-acetyl-sn-glyceryl-3 phosphorylcholine (Hanahan D.J., et al., *J. Biol. Chem.* 55:5514, 1980). Even before its chemical identification, PAF had been linked to various biological activities and pathways making it one of the important mediators responsible for a variety of physiological processes including activation or coagulation of platelets, pathogenesis of immune complex deposition, smooth muscle contraction, inflammation, hypotension, shock, pain, edema as well as respiratory, cardiovascular and intravascular alterations. Since these physiological processes are int turn associated with a large group of diseases, for example, inflammatory disease, cardiovascular disorder, hypotension, shock, psoriasis, allergic and skin diseases, asthma, lung edema, peptic or stomach ulcer, dental pain, and adult respiratory distress syndrome, more and more scientific investigation has been focused on the search of a PAF antagonist or inhibitor for treating or preventing these common diseases.

The compounds of the present invention are specific PAF antagonists. They are similar to a subclass of compounds called lignans which characteristically contain two phenylpropyl groups bonded at the β-carbon. Tetrahydrofuran (THF) derivatives can exist in eight different stereochemical configurations as shown in Scheme I.

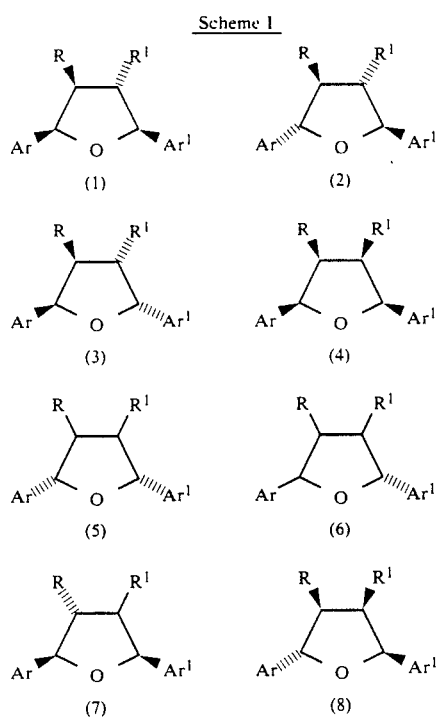

We have been able to prepare all the possible isomers of the tetrahydrofuran lignan analogs with different substituents and found that activity is stereospecific.

Accordingly, the present invention is directed to the preparation of the most potent isomers of known or novel tetrahydrofuran derivatives as PAF antagonists and use them for the treatment of various diseases including prevention of platelet aggregation, hypotension, inflammation, asthma, lung edema, adult respiratory distress syndrome, various shock syndromes, cardiovascular disorders and other related skeletal muscular disorders, graft host rejection, nephritis, pancreatitis, and lupus.

The present invention is also directed to acceptable pharmaceutical compositions containing one or more of the tetrahydrofuran derivatives and/or analogs as the active ingredient. As PAF antagonists, these novel compositions should be effective in the treatment of various skeletal muscular related diseases.

The present invention is also directed to a method of treatment comprising the administration of a therapeutically sufficient amount of these PAF antagonists to a patient suffering from various skeletal muscular disorders including inflammation, e.g., osteoarthritis, rheumatoid arthritis and gout, hypotension, shock, psoriasis, allergic or skin diseases, asthma, pain especially dental pain, peptic or stomach ulcer, lung edema, adult respiratory distress syndrome or cardiovascular disorders, graft host reJection, nephritis, pancreatitis, and lupus.

BRIEF DESCRIPTION OF THE INVENTION

The present invention is directed to a specifically substituted tetrahydrofuran of the formula (I)

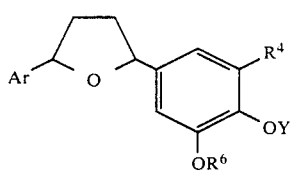

wherein Ar is a pyridyl, a dimethoxy-pyridyl or dimethoxy pyrazyl group, $R^4$ is an alkylthio, alkylsulfinyl or alkylsulfonyl containing group and at least one of the substituents at positions 3,4 or 5 contains a heterocyclic, heteroaryl or substituted phenylthio group.

DETAILED DESCRIPTION OF THE INVENTION

The present invention is directed to compounds of the following structural formula:

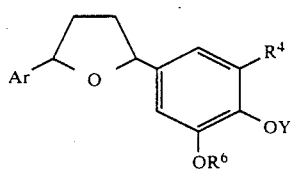

or pharmaceutically acceptable salts thereof wherein:
Ar is pyridyl, 2,3 -dimethoxypyridyl or 2,3 dimethoxypyrazyl;
  (a) $S(O)_nR^2$, in which n is 0, 1 or 2, and $R^2$ is selected from the group consisting of
    (1) $C_{1-6}$alkyl,
    (2) substituted $C_{1-6}$alkyl wherein the substituent is selected from the group consisting of hydroxy, and amino,
    (3) $C_{2-6}$alkenyl,
    (4) $C_{1-6}$alkylcarbonyl-$C_{1-16}$ alkyl, (5) N-substituted $C_{1-16}$aminoalkyl, wherein the substituent is $C_{1-16}$alkyl,
(6) N,N-di-substituted $C_{1-6}$aminoalkyl, wherein the substituents each independently represent $C_{1-16}$ alkyl,
(7) imidazolyl $C_{1-6}$alkyl,
(8) pyrrolidinyl-$C_{1-6}$alkyl,
(9) morpholinyl $C_{1-6}$alkyl,
(10) thiazolinyl-$C_{1-6}$alkyl,
(11) piperidinyl-$C_{1-6}$alkyl,
(b) imidazolylcarbonyl,
(c) morpholinylcarbonyl,
(d) morpholinyl-$C_{1-6}$alkylaminocarbonyl,
(e) N-pyrryl, and
(f) thiazolylcarbonyl;
Y is selected from the group consisting of
(a) $C_{1-12}$alkyl,
(b) substituted $C_{1-8}$alkyl wherein the substituent is selected from the group consisting of hydroxy, amino, N $C_{1-4}$ alkylamino, and N,N-di-$C_{1-4}$alkylamino,
(c) $C_{1-8}$alkoxy-$C_{1-16}$alkyl,
(d) $C_{2-6}$alkenyl,
(e) $C_{1-6}$alkyl S(O)$_m$-$C_{1-6}$ in which m is 0, 1 or 2,
(f) pyridyl $C_{1-6}$alkyl,
(g) pyridylthio-$C_{1-6}$alkyl,
(h) morpholinyl-$C_{1-6}$alkyl,
(i) hydroxyphenylthio-$C_{1-6}$alkyl,
(j) cyanophenylthio-$C_{1-6}$alkyl,
(k) imidazolylthio-$C_{1-6}$alkyl,
(l) triazolylthio-$C_{1-6}$alkyl,
(m) triazolylphenylthio-$C_{1-6}$alkyl,
(n) tetrazolylthio-$C_{1-6}$alkyl,
(o) tetrazolylphenylthio-$C_{1-6}$alkyl,
(p) aminophenylthio-$C_{1-6}$alkyl,
(q) N,N-di-substituted aminophenylthio-$C_{1-6}$alkyl wherein the substituents each independently represent $C_{1-6}$alkyl,
(r) amidinophenylthio-$C_{1-6}$alkyl,
(s) phenylsulfinyl $C_{1-6}$alkyl, and
(t) phenylsulfonyl $C_{1-6}$alkyl;
$R^6$ is selected from the group consisting of
(a) $C_{1-6}$alkyl,
(b) substituted $C_{1-6}$alkyl wherein the substituent is selected from the group consisting of hydroxy and amino,
(c) $C_{1-6}$alkyl-O-$R^{10}$, wherein $R^{10}$ is
(1) —PO$_2$(OH)$^-$M$^+$ wherein M$^+$ is a pharmaceutically acceptable cation,
(2) —C(O)(CH$_2$)$_2$—CO$_2^-$M$^+$, or
(3) —SO$_3^-$M$^+$,
(d) $C_{1-6}$-alkylcarbonyl-$C_{1-6}$alkyl,
(e) $C_{1-6}$carboxyalkyl,
(f) $C_{1-4}$alkylamino-$C_{1-6}$alkyl,
(g) N,N-di-substituted $C_{1-6}$aminoalkyl wherein the substituents each independently represent $C_{1-6}$alkyl,
(h) pyridyl-$C_{1-6}$alkyl,
(i) imidazolyl-$C_{1-6}$alkyl,
(j) imidazolyl X-$C_{1-6}$ wherein X is thio or amino,
(k) morpholinyl-$C_{1-6}$alkyl,
(l) pyrrolidinyl-$C_{1-6}$alkyl,
(m) thiazolinyl-$C_{1-6}$alkyl,
(n) piperidinyl-$C_{1-6}$alkyl,
(o) morpholinyl-$C_{1-6}$hydroxyalkyl,
(p) N-pyrryl,
(q) piperazinyl $C_{1-6}$alkyl,
(r) N substituted piperazinyl-$C_{1-6}$alkyl, wherein the substituent is $C_{1-4}$alkyl,
(s) triazolyl-$C_{1-6}$alkyl,
(t) tetrazolyl $C_{1-6}$alkyl,
(u) tetrazolylamino-$C_{1-6}$alkyl, and
(v) thiazolyl-$C_{1-6}$alkyl,
provided that at least one of $R^4$, Y and $R^6$ contains a heterocyclic, heteroaryl or a substituted phenylthio moiety.

As will be understood by those skilled in the art, pharmaceutically acceptable salts are intended to include but is not limited to salts with an inorganic acid such hydrochloride, sulfate, phosphate, diphosphate, hydrobromide and nitrate or salts with an organic acid such as malate, maleate, fumerate, tartrate, succinate, citrate, acetate, lactate, methanesulfonate, p-toluenesulfonate, palmoate, salicylate and stearate. Similarly pharmaceutically acceptable cations are intended to include but is not limited to sodium, potassium, calcium, lithium, aluminum and ammonium.

One embodiment of the present invention are the compounds of formula (I) wherein the substituents at positions 2 and 5 of the tetrahydrofuran are in a trans relationship to one another and
$R^6$ is a substituted heterocyclic or heteroaryl selected from the group consisting of
(a) pyridyl-$C_{1-6}$ alkyl,
(b) imidazolyl $C_{1-6}$alkyl,
(c) imidazolyl X $C_{1-6}$alkyl wherein X is thio or amino,
(d) morpholinyl-$C_{1-6}$alkyl,
(e) pyrrolidinyl-$C_{1-6}$alkyl,
(f) morpholinyl $C_{1-6}$alkyl,
(g) thiazolinyl-$C_{1-6}$alkyl,
(h) piperidinyl-$C_{1-6}$alkyl,
(i) morpholinyl-$C_{1-6}$hydroxyalkyl,
(j) N-pyrryl,
(k) piperazinyl $C_{1-6}$alkyl,
(l) N-substituted piperazinyl-$C_{1-6}$alkyl, wherein the substituent is $C_{1-4}$alkyl,
(m) triazolyl-$C_{1-6}$alkyl,
(n) tetrazolyl-$C_{1-6}$alkyl,
(o) tetrazolylamino-$C_{1-6}$alkyl, and
(p) thiazolyl-$C_{1-6}$alkyl.

Illustrating this embodiment is the class of compounds of the formula (I) wherein $R^4$ is S(O)$_n$$R^2$, n is 2 and $R^2$ is selected from the group consisting of
(a) $C_{1-6}$alkyl,
(b) substituted $C_{1-6}$alkyl wherein the substituent is selected from the group consisting of hydroxy, oxo and amino,
(c) N-substituted $C_{1-6}$aminoalkyl, wherein the substituent is $C_{1-6}$alkyl, and
(d) N-di-substituted $C_{1-6}$aminoalkyl, wherein the substituents each independently represent $C_{1-6}$alkyl.

A subclass of these compounds is the compounds of formula (I) wherein Y is $C_{1-12}$alkyl or hydroxy $C_{1-8}$ alkyl.

A smaller subclass of these compounds is the compounds of formula (I) wherein $R^6$ is selected from the group consisting of
(a) pyridyl $C_{1-6}$alkyl.
(b) imidazolyl-$C_{1-6}$alkyl,
(c) imidazolyl-X-$C_{1-6}$alkyl wherein X is thio or amino,
(d) morpholinyl-$C_{1-6}$alkyl,
(e) morpholinyl-$C_{1-6}$hydroxyalkyl,
(f) thiazolyl-$C_{1-6}$alkyl,
(g) piperazinyl-$C_{1-6}$alkyl, (h) pyrrolidinyl-$C_{1-6}$alkyl, and
(i) piperidinyl-$C_{1-6}$alkyl.

A still smaller subclass of these compounds is the compounds of formula (I) wherein $R^2$ is selected from the group consisting of
(a) $C_{1-3}$alkyl,
(b) $C_{1-3}$alkylcarbonyl-$C_{1-3}$alkyl,
(c) hydroxy $C_{1-4}$alkyl; and
Y is n-propyl.

Exemplifying this subclass are those compounds of the formula (I) which are:
(a) trans 2-[3-n-propylsulfonyl-4-n-propoxy-5-(2-[1-morpholino]ethoxy)phenyl]-5-[5-(2,3-dimethoxy)-pyridyl]tetrahydrofuran,
(b) trans-2-(3-n Propylsulfonyl-4-n-propoxy-5-(3-[1-morpholino]propoxy]phenyl)-5-[5 (2,3-dimethoxy) pyridyl]tetrahydrofuran,
(c) trans-2-[3-n-Propylsulfonyl-4-n-propoxy-5-(3-[1-imidazolyl]propoxy) phenyl]-5-[5-(2,3-dimethoxy)-pyridyl]tetrahydrofuran,
(d) trans-2-[3-n-Propylsulfonyl-4-n-propoxy 5-(2-[1-imidazolyl]ethoxy)phenyl]-5-[5-(2,3-dimethoxy)-pyridyl]tetrahydrofuran,
(e) trans-2-[3-(2 Hydroxypropyl)sulfonyl-4-n-propoxy-5-(3-[1-morpholino]propoxy) phenyl]-5-[5-(2,3-dimethoxy)pyridyl]tetrahydrofuran,
(f) trans-2-[3-(2-Hydroxypropyl)sulfonyl-4-n-propoxy-5-(2-[1-morpholino]ethoxy)phenyl]-5-[5-(2,3 dimethoxy)pyridyl]tetrahydrofuran,
(g) trans-2-[3 (2 Hydroxypropyl)sulfonyl-4-n-propoxy-5-(3 [1-imidazolyl]propoxy) phenyl]5-[5 (2,3-dimethoxy)pyridyl]tetrahydrofuran,
(h) trans-2-[3-(2 Hydroxypropyl)sulfonyl-4 -n-propoxy-5-(2-[1-imidazolyl]ethoxy)phenyl]-5 -[5-(2,3-dimethoxy)pyridyl]tetrahydrofuran
(i) trans-2-[3-(2-Oxopropyl)sulfonyl 4-n-propoxy-5-(3-[1-morpholino]propoxy) phenyl]-5-[5-(2,3-dimethoxy)pyridyl]tetrahydrofuran,
(j) trans-2-[3-(2-Oxopropyl)sulfonyl-4-n-propoxy-5 (2-[1-morpholino]ethoxy)phenyl]-5- [5-(2,3-dimethoxy)-pyridyl]tetrahydrofuran,
(k) trans-2-[3-(2-Oxopropyl)sulfonyl 4-n-propoxy 5 (3-[1-imidazolyl]propoxy) phenyl]-5-[5 (2,3 dimethoxy)-pyridyl]tetrahydrofuran,
(l) trans-2-[3-(2-Oxopropyl)sulfonyl 4-n-propoxy -5-(2-[1-imidazolyl]ethoxy)phenyl]-5-[5-(2,3-dimethoxy)-pyridyl]tetrahydrofuran,
(m) trans-2-[3-n Propylsulfonyl 4-n-propoxy-5-(3-[1-morpholino]propoxy) phenyl]-5-[6-(2,3-dimethoxy)-pyrazyl]tetrahydrofuran,
(n) trans-2-[3-n-Propylsulfonyl-4-n-propoxy-5-(2 [1-morpholino]ethoxy)phenyl]-5-[6-(2,3-dimethoxy)-pyrazyl]tetrahydrofuran,
(o) trans-2-[3-n-Propylsulfonyl-4-n-propoxy -5 (3-[1 imidazolyl]propoxy) phenyl]-5-[6 (2,3 dimethoxy)-pyrazyl]tetrahydrofuran,
(p) trans-2-[3-n-Propylsulfonyl-4-n-propoxy -5-(2-[1-imidazolyl]ethoxy) phenyl]-5-[6-(2,3-dimethoxy)-pyrazyl]tetrahydrofuran,
(q) trans-2-[3-(2 Hydroxypropyl)sulfonyl-4-n-propoxy-5-[3-(1-morpholino)propoxy]phenyl]5-[6-(2,3 dimethoxy)pyrazyl]tetrahydrofuran,
(r) trans-2-[3-(2-Hydroxypropyl)sulfonyl 4-n-propoxy 5-[2 (1-morpholino)ethoxy]phenyl]-5 -[6-(2,3 dimethoxy)pyrazyl]tetrahydrofuran
(s) trans-2-[3-(2-Hydroxypropyl)sulfonyl-4-n propoxy 5 [3 (1-imidazolyl)propoxy]phenyl]-5-[6-(2,3-dimethoxy)pyrazyl]tetrahydrofuran
(t) trans-2-[3-(2-Hydroxypropyl)sulfonyl-4-n-propoxy-5-[2-(1 imidazolyl)ethoxy]phenyl]-5-[6 (2,3 dimethoxy)pyrazyl]tetrahydrofuran,
(u) trans-2-[3-(2-oxopropyl)sulfonyl-4-n-propoxy-5-[3-(1-morpholino)propoxy]phenyl]-5-[6-(2,3-dimethoxy)pyrazyl]tetrahydrofuran,
(v) trans-2-[3-(2-Oxopropyl)sulfonyl 4-n-propoxy-5-[-2-(1-morpholino)ethoxy]phenyl] -5 [6-(2,3-dimethoxy)pyrazyl]tetrahydrofuran,
(w) trans-2-[3-(2 Oxopropyl)sulfonyl 4-n-propoxy-5-[3-(1 imidazolyl)propoxy]phenyl]- 5-[6-(2,3 dimethoxy)-pyrazyl]tetrahydrofuran, and
(x) trans-2-[3-(2-Oxopropyl)sulfonyl-4-n-propoxy-5-[2-(1-imidazolyl)ethoxy]phenyl]-5-[6-(2,3-dimethoxy)-pyrazyl]tetrahydrofuran, and their stereochemical isomers in the (2S,5S) configuration.

Particularly exemplifying this subclass are those compounds of the formula (I) which are:
(a) trans-2-[3-(2-Hydroxypropyl)sulfonyl-4-n-propoxy-5 (3 [1 morpholino]-2-hydroxy-propyl)phenyl]-5-[5-(2,3-dimethoxy) pyridyl]tetrahydrofuran.
(b) trans-2-[3-(2-Hydroxypropyl)sulfonyl-4-n-propoxy-5-(3-[1-morpholino]propoxy) phenyl]-5-[5-(2,3-dimethoxy)pyridyl]tetrahydrofuran,
(c) trans-2-[3-(2-Oxopropyl)sulfonyl-4-n-propoxy -5 (3-[1-morpholino]propoxy) phenyl]-5-[5-(2,3 dimethoxy)pyridyl]tetrahydrofuran,
(d) trans-2-[3-(2-Hydroxypropyl)sulfonyl-4-n-propoxy -5-(3-[1-imidazolyl]propoxy) phenyl]-5-[5-(2,3-dimethoxy)pyridyl]tetrahydrofuran,
(e) trans-2-[3-(2-Oxopropyl)sulfonyl-4-n-propoxy-5 (3 [1-imidazolyl]propoxy) phenyl]-5-[5-(2,3-dimethoxy)-pyridyl]tetrahydrofuran,
(f) trans-2-[3-(2-oxopropyl)sulfonyl 4-n-propoxy -5-[3-(1-morpholino)propoxy]phenyl]-5-[6-(2,3-dimethoxy)pyrazyl]tetrahydrofuran, and
(g) trans-2-[3-(2-Oxopropyl)sulfonyl 4-n-propoxy -5-[3-(1-imidazolyl)propoxy]phenyl]-5-[6-(2,3-dimethoxy)-pyrazyl]tetrahydrofuran.

A second embodiment of the present invention are the compounds of formula (I) wherein the substituents at positions 2 and 5 of the tetrahydrofuran are in a trans relationship to one another, and
$R^4$ is a substituted heterocyclic group selected from the group consisting of
(a) $S(O)_nR^2$, in which n is 2, and $R^2$ is
 (1) imidazolyl-$C_{1-6}$alkyl,
 (2) pyrrolidinyl-$C_{1-6}$alkyl,
 (3) morpholinyl-$C_{1-6}$alkyl,
 (4) thiazolinyl-$C_{-1-6}$alkyl,
 (5) piperidinyl-$C_{1-6}$alkyl, or
(b) imidazolylcarbonyl,
(c) morpholinylcarbonyl,
(d) morpholinyl-$C_{1-6}$alkylaminocarbonyl
(e) N-pyrryl, and
(f) thiazolylcarbonyl.

Illustrating this embodiment is the class of compounds of the formula (I) wherein $R^6$ is
$R^6$ is selected from the group consisting of
(a) $C_{1-6}$alkyl,
(b) substituted $C_{1-6}$alkyl wherein the substituent is selected from the group consisting of hydroxy and amino,
(c) $C_{1-6}$alkylcarbonyl-$C_{1-6}$alkyl,
(d) $C_{1-6}$carboxyalkyl, and
(e) $C_{1-4}$dialkylamino-$C_{1-6}$alkyl.

A subclass of these compounds is the compounds of formula (I) wherein $R^4$ is $S(O)_nR^2$, in which n is 2, and $R^2$ is
(a) pyrrolidinyl-$C_{1-6}$alkyl, or
(b) morpholinyl-$C_{1-6}$; and
Y is $C_{1-6}$alkyl.

A smaller subclass of these compounds is the compounds of formula (I) wherein $R^6$ is selected from the group consisting of
(a) $C_{1-3}$alkyl,
(b) hydroxy $C_{1-4}$alkyl; and
Y is ethyl or n propyl.

A third embodiment of the present invention are the compounds of formula (I) wherein the substituents at positions 2 and 5 of the tetrahydrofuran are in a trans relationship to one another, and
Y is a substituted heterocyclic group selected from the group consisting of
(a) pyridyl-$C_{1-6}$alkyl,
(b) pyridylthio-$C_{1-6}$alkyl,
(c) morpholinyl $C_{1-6}$alkyl,
(d) hydroxyphenylthio-$C_{1-6}$alkyl,
(e) cyanophenylthio-$C_{1-6}$alkyl,
(f) imidazolylthio-$C_{1-6}$alkyl,
(g) triazolylthio-$C_{1-6}$alkyl,
(h) triazolylphenylthio-$C_{1-6}$alkyl,
(i) tetrazolylthio-$C_{1-6}$alkyl,
(j) tetrazolylphenylthio-$C_{1-6}$alkyl,
(k) aminophenylthio-$C_{1-6}$alkyl,
(l) $C_{1-6}$dialkylaminophenylthio-$C_{1-6}$alkyl
(m) amidinophenylthio-$C_{1-6}$alkyl,
(n) phenylsulfinyl $C_{1-6}$ alkyl, and
(o) phenylsulfonyl $C_{1-6}$alkyl.

Illustrating this embodiment is the class of compounds of the formula (I) wherein
$R^4$ is $S(O)_nR^2$, n is 2 and $R^2$ is selected from the group consisting of
(a) $C_{1-6}$alkyl,
(b) substituted $C_{1-6}$alkyl wherein the substituent is hydroxy or amino,
(c) $C_{2-6}$alkenyl,
(d) $C_{1-6}$alkylcarbonyl-$C_{1-6}$alkyl, and
(e) $C_{1-6}$diaminoalkyl.

A subclass of these compounds is the compounds of formula (I) wherein $R^6$ is selected from the group consisting of
(a) $C_{1-6}$alkyl,
(b) substituted $C_{1-6}$ wherein the substituent is hydroxy or amino,
(c) $C_{1-6}$alkylcarbonyl-$C_{1-6}$alkyl,
(d) $C_{1-6}$carboxyalkyl, and
(e) N,N-disubstituted $C_{1-6}$alkyl wherein the substituents each independently represent $C_{1-6}$alkyl.

A smaller subclass of these compounds is the compounds of Formula (I) wherein Y is selected from the group consisting of
(a) pyridylthio-$C_{1-6}$alkyl,
(b) hydroxyphenylthio-$C_{1-6}$alkyl,
(c) cyanophenylthio-$C_{1-6}$alkyl,
(d) imidazolylthio-$C_{1-6}$alkyl,
(e) triazolylthio-$C_{1-6}$alkyl,
(f) tetrazolylphenylthio-$C_{1-6}$alkyl,
(g) N,N-disubstituted aminophenylthio $C_{1-6}$ alkyl, wherein the substituents each independently represent $C_{1-6}$alkyl,
(h) amidinophenylthio-$C_{1-6}$alkyl, and
(i) phenylsulfonyl $C_{1-6}$ alkyl.

A still smaller subclass of these compounds is the compounds of formula (I) wherein $R^2$ is selected from the group consisting of
(a) $C_{1-6}$alkyl,
(b) substituted $C_{1-6}$alkyl wherein the substituent is hydroxy, and
(c) $C_{1-6}$alkylcarbonyl $C_{1-6}$alkyl; and
$R^6$ is selected from the group consisting of
(a) $C_{1-6}$alkyl,
(b) substituted $C_{1-6}$alkyl wherein the substituent is hydroxy, and
(c) $C_{1-6}$alkylcarbonyl $C_{1-6}$alkyl.

The compounds of formula I may be prepared by the methods shown in the following reaction schemes wherein $R^2$, Y, and $R^6$ are defined above, unless otherwise indicated. Also, as will be evident to those skilled in the art and as demonstrated in the examples reactive groups such as amino, hydroxy, carboxy, etc. may be protected by standard methods and subsequently deprotected when it is appropriate.

REACTION SCHEME A
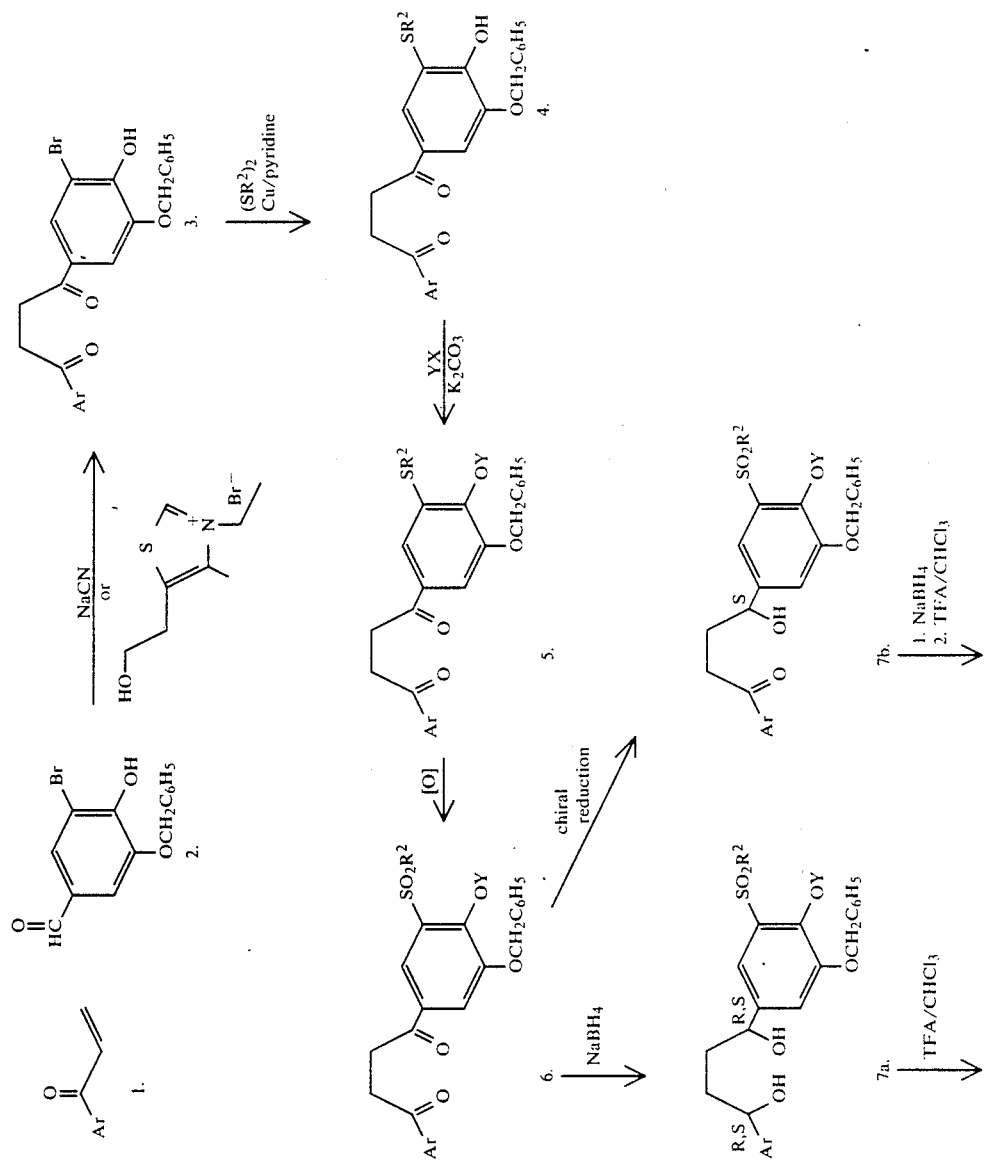

-continued
REACTION SCHEME A
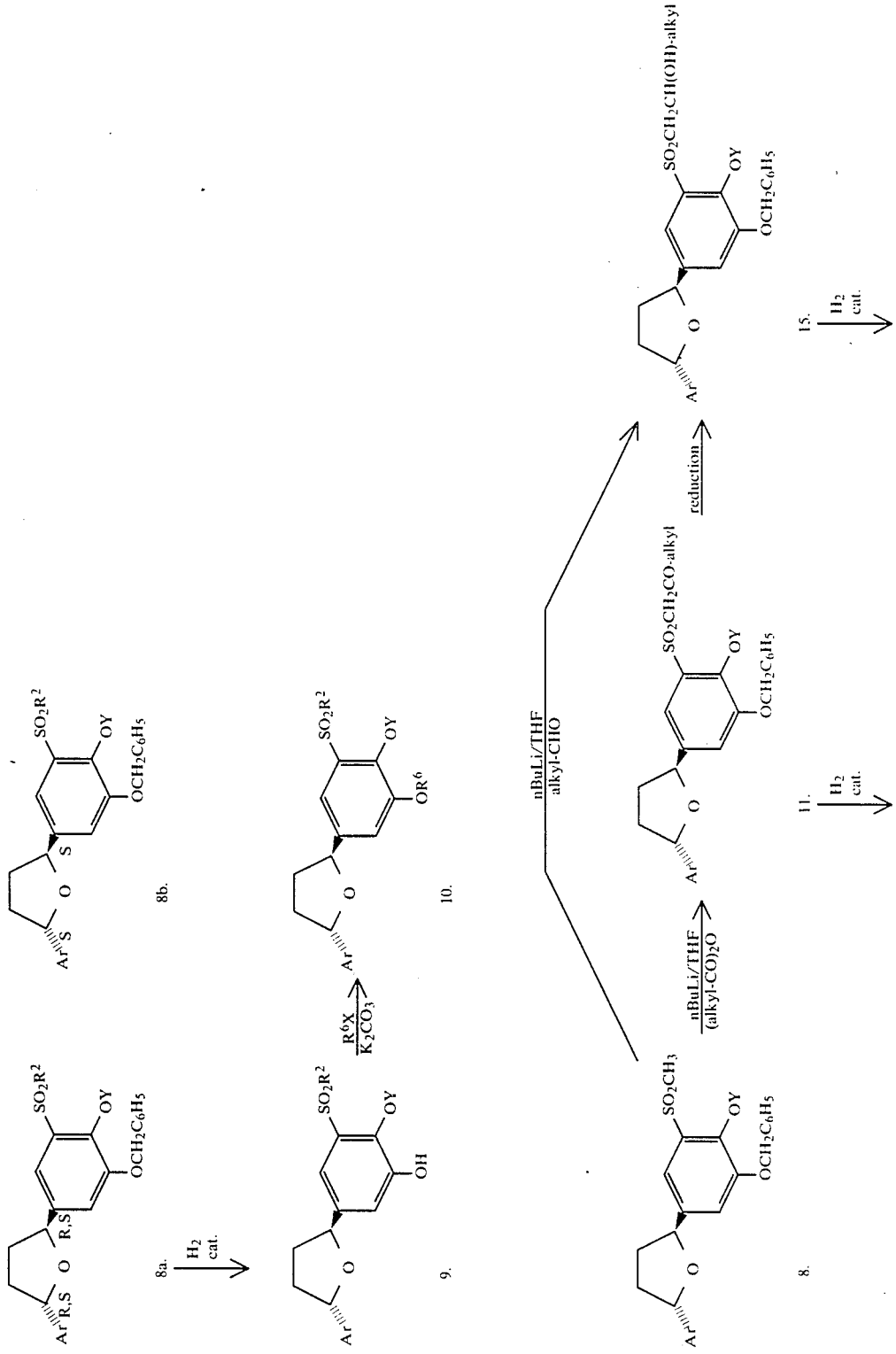

5,001,123
-continued
REACTION SCHEME A
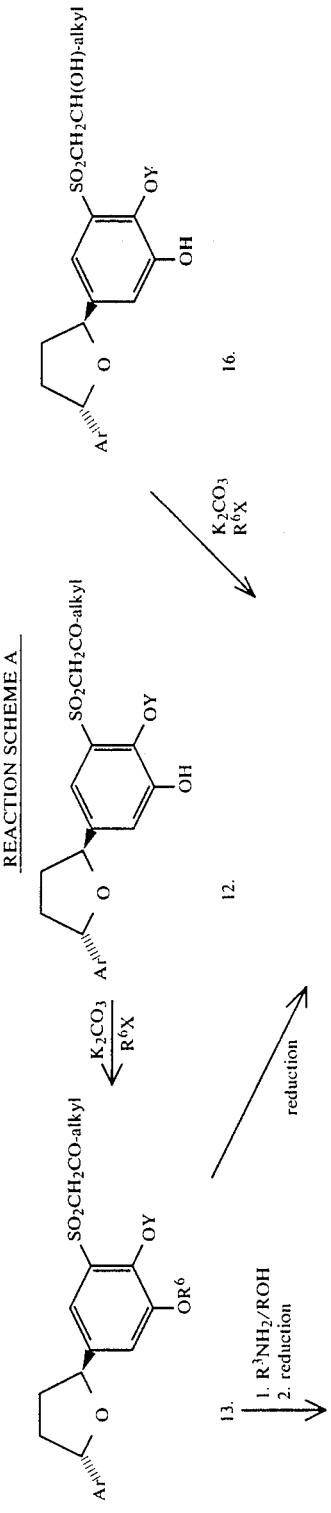
ALTERNATE DIKETONE PREPARATION
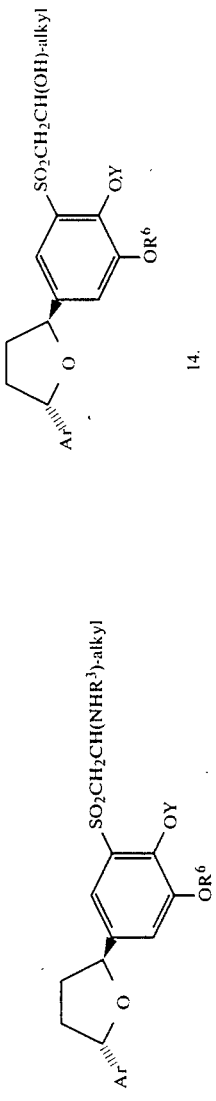
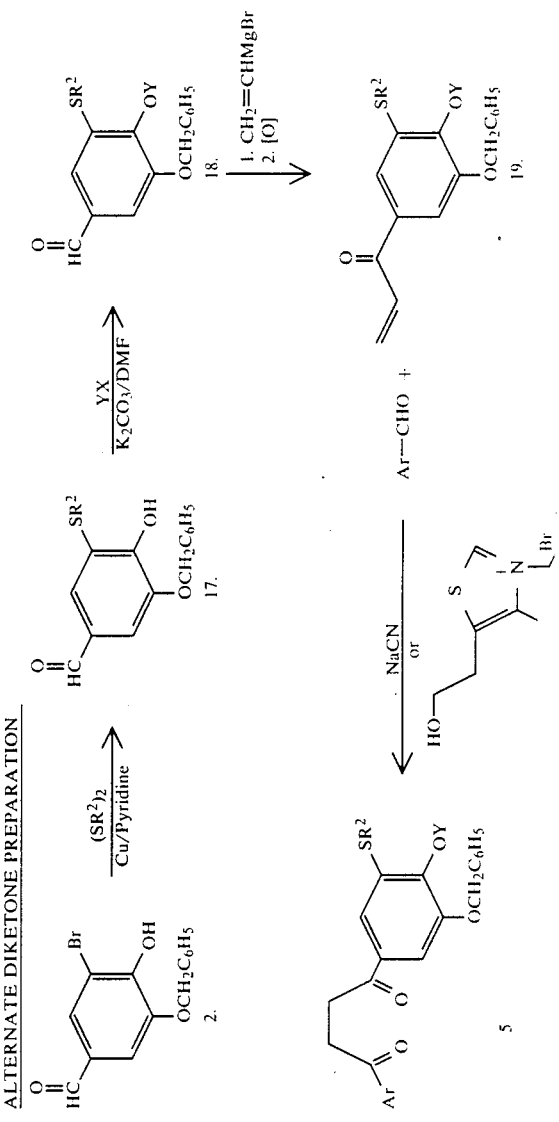

REACTION SCHEME B

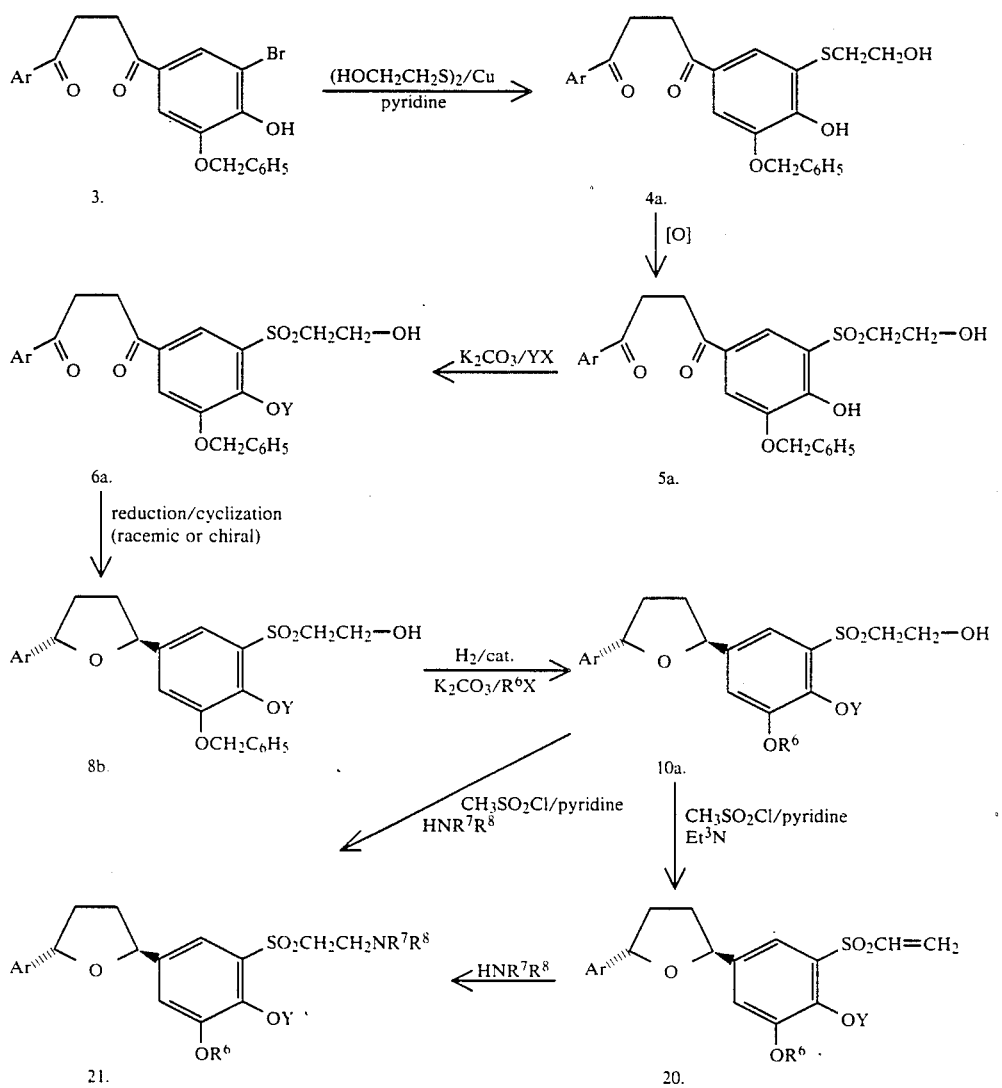

Scheme A

The compounds of formula I ma be prepared according to a sequence beginning with 5-benzyloxy-3-bromo 4-hydroxybenzaldehyde 1 which can be prepared according to the procedures outlined by J. Thiem [J. Chem. Soc. Perkin I, 1186–1190 (1977)]. One of several alternative approaches to preparing Diketone 3 is by reacting aldehyde 2 with vinylketone 1 and a base such as triethylamine with a catalytic amount of cyanide ion in DMF or 3-ethyl-5-(2-hydroxyethyl)-4-methylthiazolium bromide in DMF. Vinylketone 1 may be prepared from an arylmethylketone via conversion to a Mannich base, quaternization and elimination by standard procedures. Alternatively, the vinyl ketone may be prepared by addition of a vinyl nucleophile such as vinylmagnesium bromide to an arylaldehyde followed by oxidation of the alcohol to a ketone using a reagent such as manganese dioxide. Diketone 3 is reacted with the appropriate disulfide $(SR^2)_2$, and copper powder in pyridine at elevated temperatures to provide compound 4. The 4-position may then be derivatized by alkylation with the appropriate alkylhalide, mesylate, or tosylate Y X, using a base such as $K_2CO_3$ in a suitable solvent such as dimethylformamide (DMF) or tetrahydrofuran (THF) to provide compound 5. Alternatively, it is possible to prepare compound 5 by reversing the order of the last two steps. Oxidation of the sulfide group of compound 5 with an oxidizing agent such as m-chloroperoxybenzoic acid (mCPBA) in methylene chloride ($CH_2Cl_2$) provides sulfone 6. It is sometimes convenient to prepare diketone 5 via an alternate route beginning with preparation of arylvinylketone 19. This compound may be prepared by reacting aldehyde 2 with the appropriate disulfide $(SR^2)_2$, and copper powder in pyridine at elevated temperatures to provide compound 17. The 4-position may then be derivatized by alkylation with the appropriate alkylhalide, mesylate, or tosylate Y X, using a base such as $K_2CO_3$ in a suitable solvent such as dimethylformamide (DMF) or tetrahydrofuran (THF) to provide compound 18. Alternatively, it is possible to prepare compound 18 by reversing the order of the last two steps. Aldehyde 18 may then be reacted with vinylmagnesium bromide followed by oxidation to give arylvinylketone 19 which is then converted to diketone 5 by procedures previously described.

Furan 8a is prepared via reduction of diketone 6 with reducing agents such as sodium borohydride (NaBH₄) in ethyl alcohol (EtOH) a mixture of THF and methanol (CH₃OH) at elevated temperatures, or lithium aluminum hydride (LiAlH₄) in diethylether or THF at 0° C. Alternative methods include catalytic reduction using hydrogen and catalysts such as palladium, platinum, or rhodium. The resulting dialcohol 7a is dissolved in chloroform (CHCl₃) and carefully reacted with a dilute solution of trifluoroacetic acid (TFA) in CHCl₃ at 0° C. If adequate care is taken with this reaction the trans furan 8a is produced as the major product and can be separated from the cis diastereomer by chromatography on silica gel normally eluting with a mixture of hexanes and ethyl acetate. Alternative methods of furan formation from 7a include such reagents as methanesulfonyl chloride triethylamine or triphenylphosphine dibromide. The desired trans isomer 8a is usually a less polar material than the cis isomer on silica gel. The usually preferred chiral (S,S)-enantiomer may be prepared from diketone 6 by the specific reduction to ketoalcohol 7b using a bulky reducing agent such as lithiumtri t-butoxyaluminumhydride [LiAlH(OtBu)₃], or controlled reduction with NaBH₄. Ketoalcohol 7b can be chemically resolved via the its 3 0-methylmandelate esters to provide chiral (S) ketoalcohol 7b. Alternatively, compound 7b can be prepared in the chiral (S) form by using a chiral reducing agent such as the lithiumaluminumhydride-(S)-(-)-1,1'-bi 2-naphthol complex in THF normally at −78° C. chiral trans furan 8b is prepared by sequential reduction of the remaining keto group with NaBH₄ and cyclization with TFA as for compound 8a. The 5'-position is then derivatized by removal of the benzyl protecting group by standard deprotection methods such as hydrogenation using a catalyst such as palladium on carbon in a solvent such as methanol (MeOH), ethanol (EtOH), or ethyl acetate. The free phenol may then be alkylated with the appropriate alkylating agent $R^6X$ where X is a halide, mesylate or tosylate and a base such as K₂CO₃ in DMF, EtOH or another suitable solvent.

A variant of Scheme A is the further elaboration of compound 8a or 8b where $R^2$ is methyl. This compound may be acylated with by reaction with n-butyllithium in THF at −78° C. followed by an ester, acid chloride or anhydride such as ethyl acetate, acetylchloride or acetic anhydride to give ketosulfone 11 which can be further elaborated into compound 13 by procedures previously outlined. A further elaboration is to reduce ketosulfone 13 to hydroxysulfone 14 using a reducing agent such as NaBH₄ in EtOH, or THF and CH OH. Alternatively, compound 11 can be similarly reduced to hydroxysulfone 15 which can then be deprotected and alkylated to give 14. Alternatively, hydroxysulfone 15 can be produced directly from compound 8 by reaction with the appropriate aldehyde after reacting 8a or 8b with n-Butyllithium or a similar base. Other elaborations at position 3' may be carried out starting with compound 8a or 8b ($R^2$=CH₃, Ethyl, etc.) by procedures analogous to those described herein.

A further series of amino compounds 14a can be prepared from ketosulfone 13 or 15 by reacting them hydroxylamine or substituted amines $R^3NH_2$ in an alcoholic solvent such as ethanol (ETOH) to obtain oximes or imines. These imines or oximes may then be reduced to free or substituted amines 14a employing reducing agents such as sodium borohydride, sodium cyanoborohydride in ETOH or by catalytic hydrogenation by methods previously described.

SCHEME B

3'-(2-aminoethylsulfone) analogs (21)

A series of substituted or unsubstituted 2-aminoethylsulfone analogs 21 may be prepared by the scheme outlined in Process B. 2 hydroxyethylsulfone compounds 10a can be prepared by methods previously described and can then be derivatized as their tosylates or methanesulfonates by methods known to those in the art. Alternatively, the hydroxy group may be converted to a halide such as bromo, by one of a variety of commonly used methods such as triphenylphosphine and N-bromosuccinimide, or carbon tetrabromide or by phosphorus tribromide. Elimination to vinylsulfone 20 may be achieved by reacting the bromide, tosylate, or mesylate with a tertiary amine such as triethylamine. The vinyl sulfone 20 may then be reacted with an amine $R^7R^8NH$ in a solvent such as acetonitrile producing aminethylsulfones 21. Compounds of structure 21 may also be prepared from the precursor mesylates, etc. by reacting them directly with amines $R^7R^8NH$.

This invention also relates to a method of treatment for patients (or mammalian animals raised in the dairy, meat, or fur industries or as pets) suffering from disorders or diseases which can be attributed to PAF as previously described, and more specifically, a method of treatment involving the administration of the PAF antagonists of formula (I) as the active constituents.

Accordingly, the compounds of formula (I) can be used among other things to reduce pain and inflammation, to correct respiratory, cardiovascular, and intravascular alterations or disorders, and to regulate the activation or coagulation of platelets, to correct hypotension during shock, the pathogenesis of immune complex deposition and smooth muscle contractions.

For the treatment of inflammation such as rheumatoid arthritis, osteoarthritis, and eye inflammation, cardio-vascular disorder, asthma, shock syndrome or other diseases mediated by the PAF, the compounds of formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical comPositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy propylmethylcellulose, sodium alginate, polyvinyl pyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil in water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3 butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non irritating excipient which is solid at ordinary temperatures but liquid at the rectal temperature and will therefore melt in the rectum to release the drug. Such materials are cocoa butter and polyethylene glycols.

For topical use, creams, ointments, Jellies, solutions or suspensions, etc., containing the compounds of Formula (I) are employed.

Dosage levels of the order of from about 0.05 mg to about 140 mg per kilogram of body weight per day are useful in the treatment of the above indicated conditions (about 2.5 mg to about 7 gms. per patient per day). For example, inflammation may be effectively treated by the administration of from about 0.01 to 50 mg of the compound per kilogram of body weight per day (about 0.5 mg to about 3.5 gms per patient per day).

The amount of active ingredient that may be combined with the carrier materials to produce a single dosage form will vary depending uPon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

A representative number of compounds of the instant invention of the formula (I) exhibit in vitro antagonistic activities with respect to PAF:

The compounds of formula (I) inhibit PAF induced functions in both the cellular and tissue levels by changing the PAF binding to its specific receptor site. The ability of a compound of formula (I) to inhibit the PAF binding to its specific receptor binding site on rabbit or human platelet or PMN plasma membranes was measured by a recently developed assay.

The inhibition of $^3$[H]-PAF or $^3$[H]N-methylcarbamoyl-PAF binding to the human or rabbit platelet or PMN plasma membrane by a PAF antagonist of formula (I) was determined by a method employing isotopic labeling and filtration techniques. Generally, a series of Tris buffered solutions of the selected antagonist at predetermined concentrations were prepared. Each of these solutions contains 1 pmole of $^3$H PAF, a known amount of the test antagonist, and a sufficient amount of the pH 7.5 Tris-buffer solution (10mM Tris, 0.25% bovine serum albumin, and 150 mM NaCl per ml water) to make the final volume of 1 ml. After adding into a set of test tubes each with 100 µg of the platelet plasma membrane suspension (S.B. Hwang, et al., *Biochemistry*, Vol. 22, pp. 4756–4763, 1983) and one of the Tris buffer solutions described above, the resulting mixture in each test tube was incubated at 0° C. for about one hour or until the reaction was complete. Two control samples, one of which ($C_1$) contains all the ingredients described above except the antagonist and the other ($C_2$) contains ($C_1$) plus a 1000-fold excess of unlabeled PAF, were also prepared and incubated simultaneously with the test samples. After the incubation was completed, the contents of each test tube were filtered under vacuo through a Whatman GF/C fiberglass filter and the residue washed rapidly several times with a total of 20 ml cold (0° -5° C.) Tris buffer solution. Each washed residue was then suspended in 10 ml scintillation solution (Aquasol 2, New England Nuclear, Conn.) and the radioactivity was counted in a Packard Tri-Carb 460CD Liquid Scintillation System. Defining the counts from a test sample as "Total binding with antagonist"; the counts from the control sample $C_1$, as "Total binding $C_1$"; and the counts from the control sample $C_2$ as "non specific binding $C_2$", the percent inhibition of each test antagonist can be determined by the following equations:

$$\% \text{ Inhibition} = \frac{(\text{Total binding } C_1) - \text{Total binding with antagonist} \times 100}{\text{Specific binding}}$$

$$\text{Specific binding} = (\text{Total binding } C_1) - (\text{non-specific binding } C_2)$$

The tested compounds of formula (I) inhibit in vitro PAF-induced platelet aggregation (rabbit or human platelets); PAF-induced guinea pig peritoneal PMN (polymorphonuclear leukocytes) aggregation; PAF-induced human PMN secretion; and PAF-induced guinea pig smooth muscle contraction although they are not $H_2$ receptor antagonists. They are also shown in these inhibition studies to be highly specific to PAF. For example, they do not inhibit the binding of $H_1$ antagonist ($^3$H-pyrilamine) to guinea pig brain membrane, nor do they inhibit the binding of a cholecystokinin (CCK) receptor based on an assay on isolated rat pancreas membrane.

Furthermore, they affect no or only minute inhibition on the histamine induced ileum contraction from guinea pigs.

The antagonistic activity of representative compounds of structural formula (I) in the trans configuration is summarized in the following table.

| $R_4$ | Y | $R^6$ | % inhibition* | |
|---|---|---|---|---|
| $SO_2CH_2CH(OH)CH_3$ | $CH_2CH_2CH_3$ | $CH_2CH(OH)CH_2$-1-morpholine | 30 nM | 39% |
| | | | 3 nM | 11% |

*% inhibition of the binding of [$^3$H] N-methylcarbamoyl-PAF to human platelet membranes.

The following examples illustrate the preparation of representative compounds of this invention and Pharmaceutical compositions thereof and as such are not to be considered as limiting the invention set forth in the claims appended hereto. Further elaboration of the substituents at $R^4$, Y and $R^6$ may by found in the examples section of the application identified as Attorney Docket number 16882IE (U.S. Ser. No. 362,915 of the same title), which was filed contemporaneously with this application and is hereby incorporated by reference.

EXAMPLE 1 trans-2-[3-n-propylsulfonyl-4-n-propoxy-5-(2-[1-morpholino]ethoxy)phenyl]-5-[5-(2,3-dimethoxy) pyridyl]tetrahydrofuran

STEP 1A

3-Methylthio-4-hydroxy-5-benzoloxybenzaldehyde

A five liter flask equipped with a mechanical stirrer was charged with 100 g of 3-bromo-4-hydroxy-5-benzyloxybenzaldehyde. 80 g Cu powder, 80 mL methyldisulfide and 1.7 L pyridine, and the mixture was heated at 90° C. overnight with gentle stirring. The following day, the reaction mixture was filtered and most of the pyridine (1.3 L) was distilled off. The remaining solid residue was washed with about 2 L of methylene chloride and combined with the residue left after pyridine evaporation. The combined organic fraction was washed with 1.5 N HCl until the dark methylene chloride layer turned light brown and the aqueous layer was clear. The resulting light brown methylene chloride layer was dried over MgSO₄ and filtered through a bed of silica gel. Evaporation and crystallization from methylene chloride hexane gave 74.5 g (84%) of 2: NMR(200 MHz, CDCl₃)δ2.50(s, SCH₃), 5.20(s, OCH₂Ar), 6.72(s, OH), 7.34–7.46(m, ArH), 9.78(s, ArCHO).

STEP 1B

3 Methylthio-4-n-propoxy-5-benzyloxybenzaldehyde 64.5 g of 3-Methylthio-4-hydroxy-5-benzyloxybenzaldehyde dissolved in a 75 mL of DMF was treated with 50 g of K₂CO₃ and 32 g of 1-bromopropane and stirred overnight at 70°. The next day about 1.5 liters of methylene chloride and an equal amount of water was added to the reaction mixture. The organic layer was removed, washed three times with distilled water, dried over MgSO₄ and evaporated to yield 73 g (98%) of 3 as viscous liquid that solidified slowly: NMR(200 MHz, CDCl₃) δ1.02(t, CH₂CH₂CH₃), 1.82 (m, CH₂CH₂CH₃), 2.48(s, SCH), 4.12 (t, OCH₂CH₂OCH₃), 5.18)s, OCH₂Ar), 7.26–7.52(m, ArH), 9.86(s, ArCHO).

STEP 1C 5-(2.3-dimethoxy)pyridylvinylketone

To 100 ml of vinylmagnesium bromide (1.0 M in THF) at 0° C. was added dropwise 15.2 gm of 2,3 dimethoxypyridyl-5 carboxaldehyde dissolved in 100 ml of THF. After stirring 0.75 hours at room temperature, to the reaction mixture was carefully added 7 gm of NH₄Cl, 100 ml of H₂O and 100 ml of methylene chloride. The organic fractions were dried over MgSO₄, filtered through a thin layer of silica gel and evaporated in vacuo. The vinyl alcohol was then dissolved in 100 ml of methylene chloride and 100 ml of hexanes and to this solution was added 15 gm of MnO₂ and the reaction was stirred at room temperature until reaction was completed. The crude reaction mixture was purified by chromatography through a short column of silica gel solvent: MeCl₂/Hexanes (SO/SO) to provide 6.8 gm of the title compound. NMR (200 MHz, CDCl₃)δ³·⁹⁵⁺⁴·¹⁰ (2s, 2OCH₃), 5.94 (d, J=12+1Hz, COCH=CH₃), 6.46 (d, J=18+1Hz, COCH=CH₂), 7.14 (dd, J=16Hz+10Hz COCH=CH₂), 7.65 +8.38 (d, J=1.5Hz, ArH).

STEP 1D 1-(3-methylthio-4-propoxy-5-benzyloxyphenyl)-4-[phenyl)-4-[5-(2,3-dimethoxy) pyridyl]butan-1,4-dione 11 g 3 methylthio-4-n-propoxy-5-benzyloxybenzaldehyde, 6.8 g of 5-(2,3-dimethoxy)pyridylvinylketone, 3g of 3-ethyl-5-(2-hydroxyethyl)-4-methylthiazolium bromide, 5 mL of triethyl amine dissolved in 50 ml of dimethylformamide was heated at 60° C. overnight, and the reaction mixture was treated with 100 mL of 1.5N HCl and the aqueous layer decanted. The residue was treated again with fresh 100 mL of 1.5N HCl and decanted two more times. The remaining residue was crystallized from 400 mL of methanol and washed thoroughly with methanol, hexane, and methanol and dried to yield 8.45 g of the title compound as a crystalline solid: NMR(200 MHz, CDCl₃)δ1.04 (t, OCH₂CH₂CH₃), 1.82 (m, OCH₂CH₂CH₃), 2.48 (s, SCH₃), 3.42 (s, CO—CH₂—CH₂—CO), 3.94+4.12 (2s, 2OCH₃) 4.11 (t, OCH₂CH₂CH₃) 5.18 (s, O-CH₂—Ph) 7.30–7.50 (m, OCH₂Ph+1-ArHs) 7.63+8.52 (2d, J=1.5Hz, 4.Pyr Hs).

STEP 1E 1-(3-Methylsulfonyl-4-n-propoxy-5-benzyloxyphenyl)-4-[5-(2,3-dimethoxy)-pyridyl]butan-1,4-dione 8.45 g of 1-(³-methylthio-4-propoxy-5-benzyloxyphenyl)-4-[5-(2,3-dimethoxy) pyridyl]butan-1,4 dione dissolved in 100 mL of methylene chloride was cooled in ice bath and treated with 6 g of mCPBA (80%) in small portions. After 2–3 h of stirring, the mixture was cooled to 0° C., filtered to remove 3-chlorobenzoic acid and evaporated to a small volume. The residue obtained as such was taken up in ethyl acetate, washed with aqueous NaOH, water, brine, dried over MgSO₄ and evaporated. The residue was crystallized from methanol to yield 8.7 g of the title compound:TLC, silica gel(4:6, hexanes:ethylacetate) R_f=0.59. NMR(200 MHz, CDCl₃) NMR (200MHz, CDCl₃)δ0.99 (t, OCH₂CH₂CH₃), 1.86 (m, OCH₂CH₂CH₃), 3.30 (s, SO₂CH₃), 3.52 (s, CO—CH₂—CH₂CO), 3.92+4.12 (2s, 2OCH₂) 4.28 (t, OCH₂CH₂CH₃), 5.20 (s, O—CH₂—Ph), 7.42 (m, OCH₂Ph), 7.62+8.52 (2d, J=1.5Hz, 4Pyr Hs), 7.94+8.27 (2d, J=1.5Hz, 1ArH).

STEP 1F 1-(3-Methylsulfonyl-4-n-propoxy-5-benzyloxyphenyl)-4-[5-(2,3-dimethoxy) pyridyl]butan-1,4-diol 8.7 g of 1-(3-methylsulfonyl-4-n-propoxy-5-benzyloxyphenyl)-4-[5-(2,3-dimethoxy) pyridyl]butan-1,4-dione (STEP E) dissolved in a mixture of 80 mL dry THF and 200 mL of methanol was treated with 0.9 g of NaBH (added portionwise) at 0° C. and stirred for 3 h. The reaction mixture was then allowed to gradually warm to room temperature and stirring was continued for additional 2 h. After the completion of the reaction,(tlc, silca, 4:6, hexanes:ethylacetate) the solvent was evaporated at reduced pressure and the residue obtained as such was redissolved in 300 ml of ethyl acetate. The organic layer was washed with 1.5 N HCl, distilled water and brine respectively, and then dried over MgSO$_4$ and evaporated to yield 34.9 g of a colorless syrup which was used without further purification.

STEP 1G trans-2-(3-Methylsulfonyl-4-n-propoxy-5-benzyloxyphenyl)-5-[5-(2,3-dimethoxy)pyridyl]tetrahydrofuran 1-(3-methylsulfonyl-4-n-propoxy-5-benzyloxyphenyl)-4-[5-(2,3-dimethoxy) pyridyl]butan 1,4-diol (prepared in STEP 1F) dissolved in 100 mL of chloroform was treated dropwise with 10 ml of Trifluoroacetic acid and stirred for 16 h at 0° C. The reaction mixture was washed with 5% NaOH, water, brine, dried over MgSO$_4$ and evaporated to yield 4.5 g of a crystalline salt. 2.35 gm of the trans isomer of the title compound was crystallized from ether NMR (200 MHz, CDCl$_3$)δ1.00 (t, OCH$_2$CH$_2$CH$_3$), 1.85 (m, OCH$_2$CH$_2$CH$_3$), 2.00+2.49 (2m, 3Hs+4Hs), 3.28 (s, SO$_2$CH$_3$), 3.93+4.04 (2s, 2OCH$_3$) 4.19 (t, OCH$_2$CH$_2$CH$_3$), 5.20 (s, OCH$_2$Ar), 5.20 (s, OCH$_2$Ar), 5.20 (m 2H+SH), 7.14+7.73 (2d, J=1.5Hz, 5PyrHs), 7.36+7.54 (2d, J=1.5Hz, 2-ArHs), 7.42 (m, Ph).

STEP 1H trans-2-(3-n-Propylsulfonyl-4-n-propoxy-5-benzyloxyphenyl)-5-[5-(2,3-dimethoxy)pyridyl]tetrahydrofuran To a solution of 1 gm of trans-2-(3-methylsulfonyl-4-n-propoxy-5-benzyloxyphenyl)- 5-[5-(2,3-dimethoxy)-pyridyl]tetrahydrofuran in 7 ml of THF at −78° C. was added 1.3 ml of n-butyllithium (1.3 M solution in hexanes). After stirring for 20 min., 0.25 ml of iodoethane was added to the reaction mixture. After stirring a further 30 min., NH$_4$Cl, H$_2$O and ether were added to the reaction mixture. The combined organic fractions were dried over MgSO$_4$, evaporated to dryness and chromatographed on silica gel eluting with ethyl acetate: Hexanes 60:40 to provide 0.55 gm of the title compound. NMR (200 MHz, CDCl$_3$)δ1.02 (dt, OCH$_2$CH$_2$CH$_2$+SO$_2$CH$_2$CH$_2$CH$_3$), 1.66−1.92 (m, OCH$_2$CH$_2$CH$_3$+SO$_2$CH$_2$CH$_2$CH$_3$)2.00+2.49 (2m, 3Hs+4Hs) 3.41 (t, SO$_2$CH$_2$C$_2$CH$_3$) 3.94+4.04 (2s, SOCH$_3$) 4.18 (t, OCH$_2$CH$_2$CH$_3$) 5.20 (s, OCH$_2$Ph) 5.20 (m, 2H+5H) 7.14+7.74 (2d, J=1.5Hz, 5PyrHs) 7.36-7.52 (2d, J=1.5Hz, 2-Arhs) 7.43 (m, Ph).

STEP 1I trans-2-(3-n-Propylsulfonyl-4-n-propoxy-5-hydroxyphenyl)-5-[5-2,3-dimethoxy)pyridyl]tetrahydrofuran A solution of 0.55 gm of trans-2-(3-n-propylsulfonyl-4-n-propoxy-5-benzyloxyphenyl)-5-[5-(2,3-dimethoxy)-pyridyl]tetrahydrofuran in 60 ml of ethyl acetate and 0.1 gm of Pd/C (10%) was hydrogenated at 40 psi for 2.5 hours. The resulting reaction mixture was filtered through a thin pad of celite and evaporated in vacuo to obtain 0.5 gm of the title compound. NMR (200 MHz, CDCl$_3$)δ1.00 (t, SO$_2$CH$_2$CH$_2$CH$_3$) 1.09 (t, OCH$_2$CH$_2$CH$_3$) 1.72 (m, SO$_2$CH$_2$CH$_2$CH$_3$) 1.91 (m, OCH$_2$CH$_2$CH$_3$), 2.00 +2.49 (2m, 3Hs+4Hs) 3.34 (t, SO$_2$CH$_2$CH$_2$CH$_3$) 3.92 +4.03 (2s, 2OCH$_3$) 4.13 (t, OCH$_2$CH$_2$CH$_3$) 5.22 (t, 2H+5H) 5.65 (m, OH), 7.14+7.73 (2d, J=1.5Hz, 5-PyrHs), 7.33+7.48 (2d, J−1.5Hz, 2-ArHs).

STEP 1J trans-2-(3-n-Propylsulfonyl-4-n-propoxy-5-(2 bromoethoxy)phenyl)-5-[5-(2,3-dimethoxy)pyridyl]tetrahydrofuran To a solution of 0.5 gm of trans-2-(3-n-propylsulfonyl-4-n-propoxy-5-hydroxyphenyl)-5-[5-(2,3-dimethoxy)pyridyl]tetrahydrofuran in 20 ml of acetone was added 3 ml of 1,2-dibromoethane and 1.5 gm of finely ground K$_2$CO$_3$ and the reaction mixture was allowed to stir overnight at 55° C. The reaction mixture was then diluted with methylene chloride (50 ml) filtered and thoroughly evaporated in vacuo. To give 0.6 gm of the title compound which was used without further purification. NMR (200 MHz, CDCl$_3$)δ1.00 (t, SO$_2$CH$_2$CH$_2$CH$_3$), 2.02+2.50 (2m, 3Hs+4Hs) 3.40 (t, SO$_2$CH$_2$CH$_2$CH$_3$), 3.72 (t, OCH$_2$CH$_2$Br), 3.91+4.03 (2s, 2OCH$_3$) 4.20 (t, OCH$_2$CH$_2$CH$_2$CH$_3$)4.41 (t, OCH$_2$CH$_2$Br), 5.22 (m, 2H+5H) 7.12+7.73 (2d, J=1.5Hz, 5-PyrHs) 7.25+7.53 (2d, J=1.5Hz, 2 ArHs).

STEP 1K trans-2-[3-n-propylsulfonyl-4-n-propoxy-5-(2-[morpholino]ethoxy)phenyl-5-[5-(2,3-dimethoxy) pyridyl]tetrahydrofuran The title compound can be prepared by stirring a solution of trans-2-(3-n-propylsulfonyl-4-n propoxy-5-(2-bromethoxy)phenyl)-5-[5-(2,3-dimethoxy)pyridyl[tetrahydrofuran, prepared in step 1J with basic alumina, or K$_2$CO$_3$ , and excess morpholine in acetonitrile or acetone at 40–60° C.

EXAMPLE 2 trans-2-(3-n-Propylsulfonyl-4-n-propoxy-5-(2-bromopropoxy)phenyl)-5-[5-(2,3-dimethoxy)-pyridyl]tetrahydrofuran The title compound can be prepared according to procedures outlined in Step 1J.

From procedures outlined in Example 1, the following compounds can be prepared.

EXAMPLE 2A trans-2-(3 n Propylsulfonyl-4-n-Propoxy-5-(3-[1-morpholino)-propoxy]phenyl)-5-[5-(2,3-dimethoxy)pyridyl]tetrahydrofuran

EXAMPLE 2B trans-2-[3-n-Propylsulfonyl-4-n-propoxy-5-(3-[1-piperizinyl]propoxy)phenyl]-5-[5-(2,3-dimethoxy)-pyridyl]tetrahydrofuran

EXAMPLE 2C trans-2-[3-n-Propylsulfonyl-4-n-propoxy-5-(3-[1piperidinyl]propoxy)phenyl-5-[5-(2,3-dimethoxy)-pyridyl]tetrahydrofuran

EXAMPLE 2D trans-2-[3-n-Propylsulfonyl-4-n-propoxy-5-(3-[1-pyrrolidino]propoxy)phenyl[-5-[5-(2,3-dimethoxy) pyrridyl]tetrahydrofuran

EXAMPLE 2E trans-2-[3-n-Propylsulfonyl-4-n-propoxy-5-(3-[1-imidazolyl]propoxy)phenyl]-5-[5-(2,3-dimethoxy)-pyridyl]tetrahydrofuran

EXAMPLE 2F trans-2-[3n-Propylsulfonyl-4-n-propoxy-5-(2 [1-imidazolyl]ethoxy)phenyl]-5-[5-(2,3-dimethoxy)-pyridyl]tetrahydrofuran

EXAMPLE 2G trans-2-[3-n-Propylsulfonyl-4-propoxy-5-(3-[2-imidazolylthio]propoxy)phenyl]-5-[5-(2,3-dimethoxy)-pyridyl]tetrahydrofuran

EXAMPLE 2H trans-2-[-3n-Propylsulfonyl-4-n-propoxy-5-(2-[2-imidazolylthio]ethoxy)phenyl]-5-5-(2,3-dimethoxy)pyridyl]tetrahydrofuran

EXAMPLE 3 trans-2-[3-(2-Hydroxypropyl) sulfonyl-4-n-propoxy-5-(3-1-morpholino-2-hydroxypropoxy)phenyl]-5-[5-(2,3-dimethoxy)pyridyl]tetrahydrofuran

STEP 3A trans-2-(3-(2-Hydroxypropyl) sulfonyl-4-n-propoxy-5-benzyloxyphenyl)-5-5-(2,3-dimethoxy)-pyridyl]tetrahydrofuran 2.34 gm of the title compound was prepared from trans-2-(3-methylsulfonyl-4-n-propoxy-5-benzyloxyphenyl)-5-[5-(2,3-dimethoxy)pyridyl]tetrahydrofuran according to procedures described in Example 1, Step H using acetaldehyde in place of iodoethane. NMR (200 Mhz, CDCl$_3$)δ0.98 (t, OCH$_2$CH$_2$CH$_3$)1.26 (d, SO$_2$CH$_2$CHOHCH$_3$) 1.85 (m, OCH$_2$CH$_2$CH$_3$) 2.00 +2.49 (2m, 3Hs+4Hs), 3.40-3.66 (m, SO$_2$CH$_2$CHOHCH$_3$) 3.94+4.04 (2s, 2OCH$_3$), 4.20 (m, OCH$_2$CH$_2$CH$_3$ +SO$_2$CH$_2$CHOHCH$_3$), 5.20 (s, OCH$_2$Ar) 5.20 (m, 2-CH+5-CH), 7.14+7.74 (2d, J=1.5Hz, 5-PyrHs) 7.34-7.56 (m, 2ArHs+Ph).

STEP 3B trans-2-(3-(2-hydroxypropyl)-sulfonyl-4-n-propoxy-5-hydroxyphenyl)-5-[5-(2,3-dimethoxy)pyridyl]tetrahydrofuran The title compound was prepared according to procedures described in Example 1, Step I. NMR (200 MHz, CDCl$_3$)δ1.08 (t, OCH$_2$CH$_2$CH$_3$) 1.26 (d, SO$_2$CHOHCH$_3$) 1.90 (m, OCH$_2$CH$_2$CH$_3$) 2.00+2.50 (2m, 3-CH+4CH2) 3.36-3.60 (m, SO$_2$CH$_2$CHOHCH) 3.92+4.04 (2s, 2OCH$_3$) 4.06-4.36 (m OCH$_2$CH$_2$CH$_3$-CHOHCH$_3$) 5.22 (t, 2-CH+5-CH) 6.08 (m, OH) 7.14+7.74 (2d, J=1.5Hz, S PyrHs) 7.34+7.50 (2dd, J=1.5Hz, 2-ArHs).

STEP 3C trans-2-[3-(2-Hydroxypropyl)sulfonyl-4-n-propoxy-5-(3-[1-morpholino]2-hydropropoxy)phenyl]-5-[5-(2,3-dimethoxy)pyridyl]tetrahydrofuran 100 mg of the phenol prepared in Step 3B, 100 ml epichlorohydrin, 200 mg 1C$_2$CO$_3$, 3 ml acetone rejented for 2 hrs, filtered and evaporated and the residue purified by prep TLC (EtoAc/hexane 40:60) 80 mg of this material, 200 mg basic alumina, 150 mg morpholine, 5 ml ether was stirred at room temperature. The reaction mixture was filtered and evaporated. The newly formed more polar spot (rf 0.12) was recovered by silica prep. TLC (ethyl acetate). Pertinent NMR (200 Mhz, CDCL$_3$) 1.06 (t, CH$_3$CH$_2$CH$_2$), 1.26 (d, CH$_3$CHOHCH$_2$), 3.02 (m, CH$_2$NCH$_2$), 3.78 (m, CH$_2$OCH$_2$, 3.92 and 4.04 (2s, 2OCH$_3$), 4.12 (m, ArOCH$_2$) 5.22 (m, 2-CH and 5-CH), 7.12-7.74 (m, Ar-H).

By procedures previously described can be prepared the following compounds.

EXAMPLE 4A
trans-2-[3-(2-Hydroxypropyl)sulfonyl-4-n-propoxy-5-(3[1-morpholino]proxy)phenyl]-5-[5-(2,3-dimethoxy)-pyridyl]tetrahydrofuran

EXAMPLE 4B
trans-2-[3-(2-hydroxypropyl)sulfonyl-4-n-propoxy-5-(2-1-morpholino]ethoxy)phenyl]-5-[5-(2,3-dimethoxy)-pyridyl]tetrahydrofuran

EXAMPLE 4C
trans-2-[3-(2-Hydroxypropyl)sulfonyl-4-n-propoxy-5-(4-[1-morpholino]-n-butoxy)phenyl]-5-[5-(2,3-dimethoxy)pyridyl]tetrahydrofuran

EXAMPLE 4D
trans-2-[3-(2-Hydroxypropyl)sulfonyl-4-n-propoxy-5-(3-[1-piperizinyl]propoxy)phenyl]-5-[5-(2,3-dimethoxy)pyridyl]tetrahydrofuran

EXAMPLE 4E
trans-2-[3-(2-Hydroxypropyl)sulfonyl-4-n-propoxy-5-(3-1-piperidinyl]propoxy)phenyl]-5-[5-(2,3-dimethoxy)-pyridyl]tetrahydrofuran

EXAMPLE 4F
trans-2,3-(2-Hydroxypropyl)sulfonyl-4-n-propoxy-5-(3-[1-pyrrolidino[propoxy)phenyl]-5-[5-(2,3-dimethoxy)-pyridyl]tetrahydrofuran

EXAMPLE 4G
trans-2-[3-(2-Hydroxypropyl)sulfonyl-4-n-propoxy-5-(3-[3-imidazolyl]propoxy)phenyl]-5-[5-(2,3-dimethoxy)-pyridyl tetrahydrofuran

EXAMPLE 4H
trans-2-[3-(2-Hydroxypropyl)sulfonyl-4-n-propoxy-5-(3-[2-imidazolyl)ethoxy)phenyl]-5-[5-(2,3-dimethoxy)-pyridyl]tetrahydrofuran

EXAMPLE 4I
trans-2-[3-(2-Hydroxypropyl)sulfonyl-4-n-propoxy-5-(3-[2-imidazolylthio]propoxy)phenyl]-5-[5-(2,3-dimethoxy)pyridyl]tetrahydrofuran

EXAMPLE 4J
trans-2-[3-(2-Hydroxypropyl)sulfonyl-4-n-propoxy-5-(2-[2-imidazolylthiolethoxy) phenyl]-5-[5-(2,3-dimethoxy)pyridyl tetrahydrofuran

EXAMPLE 4K
trans-2-[3-(2-Hydroxypropyl)sulfonyl-4-n-propoxy-5-(3-[3-pyridyl]propoxy)phenyl]-5-(2,3-dimethoxy)-pyridyl]tetrahydrofuran

EXAMPLE 5
trans-2-[3-(2-Oxopropylsulfonyl-4-n-propoxy5-(3-[1-morpholino]propoxy)phenyl]-5-[5-(2,3-dimethoxy)-pyridyl]tetrahydrofuran The title compound may be prepared according to the procedures outlined in Example 1 using the intermediates which were prepared by the procedures outlined here.

STEP 5A
trans-2-(3-(2-Oxopropyl)sulfonyl-4-n-propoxy-5-benzyloxyphenyl)-5-[5-(2,3-dimethoxy)pyridyl]tetrahydrofuran 2.34 gm of the title compound was prepared from trans-2-(3-methylsulfonyl-4-n-propoxy-5-benzyloxyphenyl) 5-[5-(2,3-dimethoxy)pyridyl]tetrahydrofuran according to procedures described in Example 1, Step H using acetic anhydride in place of iodoethane. Characteristic NMR (200 MHz, CDCl$_3$)δ0.99 (t, CH$_3$CH$_2$CH$_2$), 2.36 (s, CH$_3$CO), 3.92 and 4.02 (2s, 2OCH$_3$), 4.48 (s, CH$_3$CoCH$_2$), 7.1–7.7 (m, Ar-H).

STEP 5B
trans-2-[3-(2-Oxopropylsulfonyl-4-n-propoxy-6-hydroxypenyl]-5-[5-(2,3-dimethoxy)pyridyl]tetrahydrofuran The title compound was prepared according to procedures outlined in STEP 2I. NMR (200 MHz, CDCl$_3$)δ1.06 (t, CH$_3$CH$_2$CH$_2$), 2.39 (s, CH$_3$CO), 3.93+4.03 (2s, 2OCH$_3$), 4.16 and 4.23 (2t, OCH$_2$CH$_2$) 4.28 (s, CH$_3$COCH$_2$), 5.20 (m, 2-CH+5-CH), 7.1 7.72 (Ar-H).

STEP 5C
trans-2-[3-(2-Oxopropyl)sulfonyl-4-n-propoxy-5-(3-1-morpholino]propoxy)phenyl]5-[5-(2,3-dimethoxy)-pyridyl]tetrahydrofuran The title compound can be prepared from trans-2-[3-(2-oxopropyl)sulfonyl-4-n- propoxy-5-hydroxyphenyl]-5-[5-(2,3-dimethoxy) pyridyl]tetrahydrofuran by procedures described in Example 1.

The following compounds may also be prepared from trans-2-[3-(2-Oxopropyl)sulfonyl-4-n-propoxy-5-hydroxyphenyl]5-[5-(2,3-dimethoxy)pyridyl]tetrahydrofuran.

EXAMPLE 6A trans-2-[3-(2-Oxopropyl)sulfonyl-4-n-propoxy-5-(2-[1-morpholino]ethoxy)phenyl]-5-[5-(2,3-dimethoxy)-pyridyl]tetrahydrofuran

EXAMPLE 6B trans-2-[3-(2-Oxopropyl)sulfonyl-4-n-propoxy-5-(4-[1-morpholino]butoxy)phenyl]-5-[5-(2,3-dimethoxy)-pyridyl]tetrahydrofuran

EXAMPLE 6C trans-2-[3-(2-oxopropyl)sulfonyl-4-n-propoxy-5-(3[1-piperizinyl]propoxy)phenyl]-5-[5-(2,3-dimethoxy)-pyridyl]tetrahydrofuran

EXAMPLE 6D trans-2-[3-(2-Oxopropyl)sulfonyl-4-n-propoxy-5-(3-[1-piperidinyl]propoxy)phenyl]-5-[5-(2,3-dimethoxy)-pyridyl]tetrahydrofuran

EXAMPLE 6E trans-2-3-(2-oxopropyl)sulfonyl-4-n-propoxy-5-(3-[1-pyrrolidinyl propoxy)phenyl]-5-[5-(2,3-dimethoxy)pyridyl]tetrahydrofuran

EXAMPLE 6F trans-2-[3-(2-Oxopropyl)sulfonyl-4-n-propoxy-5-(3-[1-imidazolyl]propoxy)phenyl]-5-[5-(2,3-dimethoxy)-pyridyl]tetrahydrofuran

EXAMPLE 6G trans-2-[3-(2-oxopropyl)sulfonyl-4-n-propoxy-5-(2-[1-imidazolyl]ethoxy)phenyl-5-[5-(2,3-dimethoxy)-pyridyl]tetrahydrofuran

EXAMPLE 6 trans-2-[3-(2-Oxopropyl)sulfonyl-4-n-propoxy-5-(3-[2-imidazolylthio]propoxy)phenyl]-5-[5-(2,3-dimethoxy)-pyridyl]tetrahydrofuran

EXAMPLE 6I trans-2-[3-(2-oxopropyl)sulfonyl-4-n-propoxy-5-(2-[2-imidazolylthioethoxy)phenyl]5-[5-(2,3-dimethoxy)-pyridyl]tetrahydrofuran

EXAMPLE 7 trans-2-[3-n-Propylsulfonyl-4-n-propoxy-5-(3-[1-morpholino]propoxy)phenyl]-5-[6-(2,3-dimethoxy)pyrazyl]-tetrahydrofuran

STEP 7A

2-[3-dimethoxypyrazine

A solution of 22 ml of sodium methoxide in methanol (25% w/w) was added to a stirred solution of 2,3-dichloropyrazine (6.3 gm, 0.04 mol) under $N_2$ at 25° C. After stirring for 16 hours an additional 3 ml of sodium methoxide was added with stirring for an added 5 hours. The reaction mixture was diluted with methylene chloride, filtered and the filtrate was evaporated in vacuo. The residue was dissolved in methylene chloride, washed with water, dried over $MgSO_4$, filtered and evaporated to give 5.71 gm of the title compound as a crystalline solid. NMR $(CDCl_3)\delta 4.01$(s, 6H, —$OCH_3$), 7.60(s, 2H, ArH).

STEP 7B 2-bromo-5.6-dimethoxypyrazine

A solution of 14.6 gm of N-bromosuccinamide, 32 ml of dry DMF was added to a stirred solution of 11 gm (0.078 mol) of 2,3-dimethoxypyrazine in 14 ml of DMF at 0° C. whereupon the reaction was warmed to 25° C. and stirred for 16 hours. The reaction mixture was then cooled in an ice bath and to it was added aqueous $Na_2SO_3$ to remove the bromine and this was poured into ice water. The resulting crystalline solid was filtered, triturated with water and dried to give 10.48 gm of the title compound. NMR $(CDCl_3)\delta 4.0$, 4.02(2s, 6H, $OCH_3$), 7.70(s,1H).

STEP 7C 2,3-dimethoxy-5-formylpyrazine

To a stirred solution of 4.85 gm of 2-bromo 5,6-dimethoxypyrazine in 80 ml of dry ether under $N_2$ at $-35°$ C. was added dropwise 14.5 ml of n butyllithium (1.6 N in hexanes). After stirring for 0.5 hours at $-35°$ C. 5.74 ml of dry DMF was added dropwise to the reaction mixture. This dark brown homogeneous solution was stirred at $-20°$ C. for 1 hour and at 25° C. for 0.5 hours, then was quenched with an aqueous solution of $NH_4Cl$. The reaction mixture was extracted with methylene chloride, and the organic fractions were washed with water, brine and dried over $MgSO_4$, and filtered and evaporated to give a red oil. Chromatography on a short silica gel column provided 1.5 gm of a mixture of the title aldehyde and its hydrate which was used without further purification.

STEP 7D 1-(3-methylthio-4-propoxy-5-benzyloxyphenyl)-4-[6-(2,3-dimethoxy)-pyrazyl]butan-1.4-dione 1.76 gm of the title compound was prepared from 2,3-dimethoxy 5-formylpyrazine and 3-methylthio 4-propoxy 5-benzyloxyphenylvinylketone (prepared from 3-methylthio-4-n-propoxy 5-benzyloxybenzaldehyde according to procedures in Example 1, Step C.) according to procedures described in Example 1, Step D. Pertinent NMR signals: 2.48 (s,3H, $SCH_3$), 3.4,3.55(2m, 4H,C-3,C -4H)

STEP 7E trans-2-(3-n-Propylsulfonyl-4-n-propoxy-6-benzyloxyphenyl)-5-[6-(2,3-dimethoxy)-pyrazyl]-tetrahydrofuran The title compound was prepared from 1-(3-methylthio-4-propoxy-5-benzyloxy phenyl)-4-[6-(2,3-dimethoxy) pyrazyl]butan 1,4-dione according to procedures described in Example 1, Steps E - H. NMR $(CDCl_3)\delta 1.0$(2t, 6H, $CH_2CH_3$), 1.6–2.6(m, $CH_2CH_2CH_3$, C-3H,C-4H), 3.38(m,2H, $SO_2CH_2CH_2CH_3$), 4.0, 4.1(2s,6H,$OCH_3$), 4.15(t, 2$OCH_2CH_2CH_3$), 5.1–5.3(m,4H,$OCH_2Ar$, C-2H, C-5H), 7.3–7.545(m,ArH), 7.71(s, 1H, pyrazineH)

STEP 7F trans-2-[3-n-Propylsulfonyl-4-propoxy-5-(3-[1-morpholino]propoxy)phenyl-5-[6-(2,3-dimethoxy)pyrazyl]-tetrahydrofuran The title compound can be prepared from trans-2-(3-n ProPylsulfonyl 4-n proPoxy-5-benzyloxyphenyl)-5-[6-(2,3-dimethoxy)-pyrazyl]-tetrahydrofuran according to procedures described in Example 1, Steps I, and Example 2.

The following compounds can be prepared according to procedures described in Example 7.

EXAMPLE 8A trans-2-[3-n-Propylsulfonyl-4-n-propoxy-5-(2-[1-morpholino]ethoxy)phenyl]-5-[6-(2,3-dimethoxy)pyrazyl]-tetrahydrofuran

EXAMPLE 8B trans-2-[3-n-Propylsulfonyl-4-n-propoxy-5-(4-[1-morpholino]-n-butoxy)phenyl]-5-[6-(2,3-dimethoxy)-pyrazyl]tetrahydrofuran

EXAMPLE 8C trans-2-[3-n-Propylsulfonyl-4-n-propoxy-5-(3-[1-piperizinyl]propoxy)phenyl]-5-[6-(2,3-dimethoxy)-pyrazyl]tetrahydrofuran

EXAMPLE 8D trans-2-[3-Propylsulfonyl-4-n-propoxy-5-(3-[1-piperidinyl]propoxy)phenyl]-5-[6-(2,3-dimethoxy)-pyrazyl]tetrahydrofuran

EXAMPLE 8E trans-2-[3-n Propylsulfonyl-4-n-5-(3-[1-pyrrolidinyl]propoxy)-phenyl]-5-[6-(2,3-dimethoxy)pyrazyl]tetrahydrofuran

EXAMPLE 8F trans-2-[3-n-Propylsulfonyl-4-n-propoxy-5-[3-[1-imidazolyl]propoxy)phenyl]-5-6-(2,3-dimethoxy)-pyrazyl]tetrahydrofuran

EXAMPLE 8G trans-2-[3-n Propylsulfonyl-4-n-propoxy-5-(2[1-imidazolylmethoxy)phenyl]-5-[6-(2,3-dimethoxy)pyrazyl]tetrahydrofuran

EXAMPLE 8H trans-2-[3-n Propylsulfonyl-4-n-propoxy-5-(4[1-imidazolyl]butoxy)pbenyl]-5-[6-(2,3-dimethoxy)pyrazyl]tetrahydrofuran

EXAMPLE 8I trans-2-[3-n-Propylsulfonyl-4-n-propoxy-5-[3-[2-imidazolylthio]propoxy)phenyl]-5-[6-(2,3-dimethoxy)-pyrazyl]tetrahydrofuran

EXAMPLE 8J trans-2-[3-n-Propylsulfonyl-4-n-propoxy-5-(2-[2-imidazolylthio]ethoxy)phenyl]-5-[6-(2,3-dimethoxy)-pyrazyl]tetrahydrofuran

EXAMPLE 9 trans-2-[3-(2-hydroxypropyl)sulfonyl-4-n-propoxy-5-[3-(1-morpholino)propoxy]phenyl]-5-[6-(2,3-dimethoxy)-pyrazyl]tetrahydrofuran The title compound may be prepared according to procedures described in Example 4.

By similar procedures the following compounds can be prepared.

EXAMPLE 10A trans-2-[3-(2-Hydroxypropyl)sulfonyl-4-n-propoxy-5[2-(1-morpholino)ethoxy]phenyl]-5-[6-(2,3-dimethoxy)-pyrazyl]tetrahydrofuran

EXAMPLE 10B trans-2 3-(2-Hydroxypropyl)sulfonyl-4-n-propoxy-5-[4-(1-morpholino)butoxy]phenyl]-5-[6-(2,3-dimethoxy)pyrazyl]-tetrahydrofuran

EXAMPLE 10C trans-2-[3-(2-Hydroxypropyl)sulfonyl-4-n-propoxy-5-[3-(1-piperidinyl)propoxy]phenyl]-5-[6-(2,3-dimethoxy)-pyrazyl]-tetrahydrofuran

EXAMPLE 10D trans-2-[3-(2-Hydroxypropyl)sulfonyl-4-n-propoxy-5-[3-(1-pyrrolidinyl)propoxy]phenyl]-5-[6-(2,3-dimethoxy)-pyrazyl]tetrahydrofuran

EXAMPLE 10E trans-2-[3-(2-Hydroxypropyl)sulfonyl-4-n-propoxy-5-[3-(1-imidazolyl)propoxy]phenyl]-5-6-(2,3-dimethoxy)-pyrazyl]tetrahydrofuran

EXAMPLE 10F trans-2-[3-(2-Hydroxypropyl)sulfonyl 4-n (2,3-dimethoxy)pyrazyl]tetrahydrofuran

EXAMPLE 10 trans-2-[3-(2-Hydroxypropyl)sulfonyl-4-n-propoxy-5-[2-(1-imidazolyl)ethoxy]phenyl]-5-[6-(2,3-dimethoxy)-pyrazyl]tetrahydrofuran

EXAMPLE 10H trans-2-[3-(2-Hydroxypropyl)sulfonyl-4-n-propoxy-5-[3-(2-imidazolylthio)propoxy]phenyl]-5-[6-(2,3-dimethoxy)pyrazyl]tetrahydrofuran

EXAMPLE 10I trans-2-[3-(2-Hydroxypropyl)sulfonyl-4-n-5-[2-(2-imidazolylthio)ethoxy]phenyl]-5-[6-(2,3-dimethoxy)-pyrazyl]tetrahydrofuran

EXAMPLE 11

11-trans-2-[3-(2-oxopropyl)sulfonyl-4-n-propoxy-5,3-(1-morpholino)propoxy]phenyl-5-[6-(2,3-dimethoxy)-pyrazyl]tetrahydrofuran The title compound may be prepared according to procedures described in Example 5.

By similar procedures the following compounds can be prepared.

EXAMPLE 11A trans-2-[3-(2-Oxopropyl)sulfonyl-4-n-propoxy-5-[2-(1-morpholino)ethoxylphenyl]-5-[6-(2,3dimethoxy)-pyrazyl]tetrahydrofuran

EXAMPLE 11B trans-2-[3-(2-Oxopropyl)sulfonyl-4-n-propoxy-5-[4-(1-morpholino)butocyophenyl]-5-[6-(2,3-dimethoxy)-pyrazyl]tetrahydrofuran

EXAMPLE 11C trans-2-[3-(2-Oxopropyl)sulfonyl-4-n-propoxy-5-[3-(1-piperidinyl)propoxy[phenyl]-5-[6-(2,3-dimethoxy)-pyrazyl]tetrahydrofuran

EXAMPLE 11D trans-2-[3-(2-Oxopropyl)sulfonyl-4-n-propoxy-5-[3-(1-pyrrolidinyl)propoxy]phenyl]-5-[6-(2,3-dimethoxy)-pyrazyl]tetrahydrofuran

EXAMPLE 11E trans-2-[3-(2-Oxopropyl)sulfonyl-4-n-propoxy-5-[3-(1-imidazolyl)propoxy]phenyl]-5-[6-(2,3-dimethoxy)-pyrazyl]tetrahydrofuran

EXAMPLE 11F trans-2-[3-(2-Oxopropyl)sulfonyl-4-n-propoxy-5-[2-(1-imidazolyl)ethoxy]phenyl)-5-[6-(2,3-dimethoxy)-pyrazyl]tetrahydrofuran

EXAMPLE 11G trans-2-[3-(2-Oxopropyl)sulfonyl-4-n-propoxy-5-[4-(1-imidazolyl)butoxy]phenyl]-5-[6-(2,3-dimethoxy)-pyrazyl]tetrahydrofuran

EXAMPLE 11H trans-2-[3-(2-Oxopropyl)sulfonyl-4-n-propoxy-5-[3-(2-imidazolylthio)propoxy]phenyl]-5-[6-(2,3-dimethoxy)-pyrazyl]tetrahydrofuran

EXAMPLE 11I trans-2-[3-(2-oxopropyl)sulfonyl-4-n-propoxy-5-[2-(2-imidazolylthio)ethoxy]phenyl]-5-[6-(2,3-dimethoxy)-pyrazyl]tetrahydrofuran

What is claimed is:

1. A compound of the following structural formula

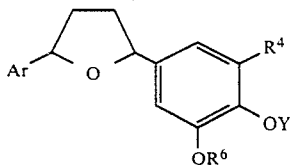

or a pharmaceutically acceptable salt t hereof wherein:
Ar is pyridyl, or 2,3-dimethoxypyridyl,
$R^4$ is
(a) $S(O)_nR^2$, in which n is 0, 1 or 2, and $R^2$ is selected from the group consisting of
(1) $C_{1-6}$alkyl,
(2) substituted $C_{1-6}$alkyl wherein the substituent is selected from the group consisting of hydroxy, and amino,
(3) $C_{2-6}$alkenyl,
(4) $C_{1-6}$alkylcarbonyl-$C_{1-6}$alkyl,
(5) N-substituted $C_{1-6}$aminoalkyl, wherein the substituent is $C_{1-6}$alkyl,
(6) N,N-di-substituted $C_{1-6}$aminoalkyl, wherein the substituents each independently represent $C_{1-6}$alkyl,
Y is selected from the group consisting of
(a) $C_{1-12}$alkyl,
(b) substituted $C_{1-8}$alkyl wherein the substituent is selected from the group consisting of hydroxy, amino, N-$C_{1-4}$alkylamino, and N,N-di-$C_{1-4}$alkylamino,
(c) $C_{1-8}$alkoxy-$C_{1-6}$alkyl,
(d) $C_{2-6}$alkenyl,
(e) $C_{1-6}$alkyl $S(O)_m$-$C_{1-6}$alkyl in which m is 0, 1 or 2, and
$R^6$ is selected from the group consisting of
(a) morpholinyl-$C_{1-6}$alkyl,
(b) pyrrolidinyl-$C_{1-6}$alkyl,
(c) thiazolinyl-$C_{1-6}$alkyl,
(d) piperidinyl-$C_{1-6}$alkyl,
(e) morpholinyl-$C_{1-6}$hydroxyalkyl,
(f) piperazinyl-$C_{1-6}$alkyl, and
(g) N-substituted piperazinyl-$C_{1-6}$alkyl, wherein the substituent is $C_{1-4}$alkyl,
provided that one of $R^4$, Y and $R^6$ contains a heterocyclic, heteroaryl or a substituted phenylthio moiety.

2. A compound of claim 1 wherein the substituents are in the trans position to one another.

3. A compound according to claim 2 wherein $R^4$ is $S(O)_nR^2$, n is 2 and $R^2$ is selected from the group consisting of
(a) $C_{1-6}$alkyl,
(b) substituted $C_{1-6}$alkyl wherein the substituent is selected from the group consistent of hydroxy, oxo and amino,
(c) N-substituted $C_{1-6}$aminoalkyl, wherein the substituent is $C_{1-6}$alkyl,
(d) N-di-substituted $C_{1-6}$aminoalkyl, wherein the substituents each independently represent $C_{1-6}$alkyl.

4. Compound according to claim 3 wherein Y is $C_{1-12}$alkyl or hydroxy $C_{1-8}$alkyl.

5. Compound according to 4 wherein $R^6$ is selected from the group consisting of
(a) morpholinyl-$C_{1-6}$alkyl,
(b) pyrrolidinyl-$C_{1-6}$alkyl,
(c) piperidinyl-$C_{1-6}$alkyl,
(d) morpholinyl-$C_{1-6}$hydroxyalkyl, and
(e) piperazinyl-$C_{1-6}$alkyl.

6. A compound according to claim 23 wherein $R^2$ is selected from the group consisting of
(a) $C_{1-3}$alkyl,
(b) $C_{1-3}$alkylcarbonyl-$C_{1-3}$alkyl, and
(c) hydroxy $C_{1-4}$alkyl; and
Y is n-propyl.

7. A compound of claim 6 which is: trans-2-[3-Hydroxypropyl)sulfonyl-4-n-propoxy-5-(3-[1-morpholino[-2-hydroxypropyl)phenyl]-5-[5-(2,3-dimethoxy) pyridyl]tetrahydrofuran.

8. A pharmaceutical composition for antagonizing the effects of PAF which comprises a nontoxic therapeutically effective amount of a compound according to claim 2 and a pharmaceutically acceptable carrier.

9. A method of antagonizing the effects of PAF in a subject in need thereof which comprises administering to said subject a nontoxic therapeutically effective amount of a compound according to claim 2.

* * * * *